US008182805B2

(12) United States Patent
Viskari et al.

(10) Patent No.: US 8,182,805 B2
(45) Date of Patent: May 22, 2012

(54) PREVENTION OF ALLERGIC SENSITIZATION

(75) Inventors: Hanna Viskari, Pirkkala (FI); Mikael Knip, Helsinki (FI); Tapio Seiskari, Siuro (FI); Heikki Hyöty, Tampere (FI); Laura Kummola, Tampere (FI); Anita Kondrashova, Tampere (FI)

(73) Assignee: Vactech Oy, Tampere (FI)

( * ) Notice: Subject to any disclaimer, the term of this patent is extended or adjusted under 35 U.S.C. 154(b) by 196 days.

(21) Appl. No.: 12/523,328

(22) PCT Filed: Jan. 31, 2008

(86) PCT No.: PCT/FI2008/050032
§ 371 (c)(1),
(2), (4) Date: Sep. 4, 2009

(87) PCT Pub. No.: WO2008/092996
PCT Pub. Date: Aug. 7, 2008

(65) Prior Publication Data
US 2010/0034848 A1 Feb. 11, 2010

(30) Foreign Application Priority Data
Feb. 1, 2007 (FI) ...................................... 20075063

(51) Int. Cl.
*A61K 39/12* (2006.01)
*A61K 39/35* (2006.01)
(52) U.S. Cl. ..................................... 424/93.3; 424/217.1
(58) Field of Classification Search ......................... None
See application file for complete search history.

(56) References Cited

FOREIGN PATENT DOCUMENTS
WO 93/11251 6/1993
WO 01/00236 1/2001

OTHER PUBLICATIONS

Finkelman et al. Journal of Allergy and Clinical Immunology, vol. 120, Issue 3, Sep. 2007, pp. 544-550.*
Schenkel et al. Expert Opinion on Pharmacotherapy, 2000, vol. 1 (7), pp. 1289-1306.*
Halperin et al. Vaccine, 2006, vol. 24, pp. 4017-4023.*
Maier et al. J. Allergy Clin. Immunol. 2006, vol. 117, No. 6, pp. 1306-1313.*
Hawa et al. Diabetes Care, 2000, vol. 23, pp. 228-233.*
McIntire, J. J., et al. "Hepatitis A virus link to atopic disease."*Nature* (2003) vol. 425, No. 6958, p. 576.
Von Hertzen, L. C., et al. "Asthma and atopy—the price of affluence?." *Allergy* (2004) vol. 59, pp. 124-137.
Lozovskaia, L. S., et al. "Chronic congenital Coxsackie virus infection in the etiology of allergic disease in children." *Voprosy Virusologii* (1999) vol. 44, No. 6, pp. 268-272, Medline [Online], EPOQUENET, AN NLM 10665063, Abstract.

Seiskari, T., et al. "Allergic sensitization and microbial load—a comparison between Finland and Russian Karelia." *Clinical and Experimental Immunology* (2007) vol. 148, No. 1, pp. 47-52.
Lee, K. K., et al. "Relationship of Early Childhood Viral Exposures to Respiratory Symptoms, Onset of Possible Asthma and Atopy in High Risk Children: the Canadian Asthma Primary Prevention Study." *Pediatric Pulmonology* (2007) vol. 42, pp. 290-297.
Destefano, F., et al. "Childhood vaccinations and risk of asthma."*The Pediatric Infectious Disease Journal* (2002), vol. 21, No. 6, pp. 498-504.
Bager, P., et al. "Age at childhood infections and risk of atopy. "*Thorax* (2002) 57, pp. 379-382.
Benn, C. S., et al. "Cohort study of sibling effect, infectious diseases, and risk of atopic dermatitis during first 18 months of life." *BJM, doi: 10.1136/bmj.38069.512245.FE* (2004) pp. 1 of 5.
Cullinan, P., et al. "Can early infection explain the sibling effect in adult atopy?"*Eur Respir J* (2003) 22: pp. 956-961.
Maria A. Curotto de Lafaille, et al. "CD4+ regulatory T cells in autoimmunity and allergy."*Current Opinion in Immunology* (2002) 14: pp. 771-778.
Gereda, J. E., et al. "Levels of Environmental Endotoxin and Prevalence of Atopic Disease."*Jama* (2000) 284(13) pp. 1652-1653.
Gereda, J. E., et al. "Relation between house-dust endotoxin exposure, type 1 T-cell development, and allergen sensitisation in infants at high risk of asthma." *The Lancet* (2000) vol. 355, pp. 1680-1683.
Isomaki, P., et al. "The expression of SOCS is altered in rheumatoid arthritis."*Rheumatology* (2007) 46: pp. 1538-1546.
Karmaus, W., et al. "Does a higher number of siblings protect against the development of allergy and asthma? A review."*Journal of Epidemiology and Community Health* (2002) 56: pp. 209-217.
Kilpelainen, M., et al. "Farm environment in childhood prevents the development of allergies."*Clinical and Experimental Allergy* (2000) vol. 30, pp. 201-208.
Kondrashova, A., et al. "A six-fold gradient in the incidence of type 1 diabetes at the eastern border of Finland." *Annals of Medicine* (2005) 37(00): 1-6.
Kosunen, T. U., et al. "Increase of allergen-specific immunoglobulin E antibodies from 1973 to 1994 in a Finnish population and a possible relationship to *Helicobacter pylori* infections." *Clinical and Experimental Allergy* (2002) 32: pp. 373-378.
Linneberg, A., et al. "IgG antibodies against microorganisms and atopic disease in Danish adults: The Copenhagen Allergy Study." *J Allergy Clin Immunol* (2003) 111: pp. 847-853.
Matricardi, P. M., et al. "Exposure to foodborne and orofecal microbes versus airborne viruses in relation to atopy and allergic asthma: epidemiological study."*BMJ* (2000) vol. 320, pp. 412-417.
Matricardi, P. M., et al. "Cross sectional retrospective study of prevalence of atopy among Italian military students with antibodies against hepatitis A virus." *BMJ* (1997) vol. 314, pp. 999-1003.

(Continued)

*Primary Examiner* — Bao Li
(74) *Attorney, Agent, or Firm* — Ladas & Parry

(57) ABSTRACT

The present invention relates to prevention and treatment of allergic sensitization and diseases associated therewith by treatment with an enterovirus vaccine, wherein the enterovirus does not contain an exogenous nucleic acid sequence that is integrated into the viral genome and that encodes an allergen that induces said allergic sensitization.

8 Claims, 2 Drawing Sheets

OTHER PUBLICATIONS

Mosmann, T. R., et al. The expanding universe of T-cell subsets: Th1, Th2 and more. *Immunology Today* (1996) vol. 17, No. 3, pp. 138-146.

Maki, M., et al. "Prevalence of Celiac Disease among Children in Finland." *The New England Journal of Medicine* (2003) 348:25, pp. 2517-2524.

Pfaffl, M. W. "JA new mathematical model for relative quantification in real-time RT-PCR." *Nucleic Acids Research* (2001) vol. 29, No. 9, pp. 2002-2007.

Polack, F. P., et al. "Atypical Measles and Enhanced Respiratory Syncytial Virus Disease (ERD) Made Simple." *Pediatric Research* (2007) vol. 62, No. 1, pp. 111-115.

Riedler, J., et al. "Austrian children living on a farm have less hay fever, asthma and allergic sensitization." *Clinical and Experimental Allergy* (2000) vol. 30, pp. 194-200.

Roivainen, M., et al. "Several Different Enterovirus Serotypes Can be Associated with Prediabetic Autoimmune Episodes and Onset of Overt IDDM." *Journal of Medical Virology* (1998) 56, pp. 74-78.

Salminen, K., et al. "Enterovirus Infections are Associated with the Induction of β-Cell Autoimmunity in a Prospective Birth Cohort Study." *Journal of Medical Virology* (2003) 69: pp. 91-98.

Strachan, D. "Hay fever, hygiene, and household size."*BMJ* (1989) vol. 299, pp. 1259-1260.

Strachan, D. P. Family size, infection and atopy: the first decade of the "hygiene hypothesis." *Thorax* (2000) 55 (Suppl 1) pp. S2- S10.

Umetsu, D. T., et al. "Regulatory T cells control the development of allergic disease and asthma."*J Allergy Clin Immunol* (2003) vol. 112, No. 3, pp. 480-487.

Vartiainen, E., et al. "Allergic diseases, skin prick test responses, and IgE levels in North Karelia, Finland, and the Republic of Karelia, Russia."*J Allergy Clin Immunol* (2002) 109: pp. 643-648.

von Hertzen, L., et al. "Growing disparities in atopy between the Finns and the Russians: A comparison of 2 generations." *J Allergy Clin Immunol* (2006) 117: pp. 151-157.

Von Mutius, E., et al. "Exposure to endotoxin or other bacterial components might protect against the development of atopy." *Clinical and Experimental Allergy* (2000) vol. 30, pp. 1230-1234.

Wu, K., et al. " IL-10-Producing Type 1Regulatory T cells and Allergy."*Cellular and Molecular Immunology* (2007) vol. 4, No. 4, pp. 269-275.

* cited by examiner

PREVENTION OF ALLERGIC SENSITIZATION

FIELD OF THE INVENTION

The present invention relates to decreasing the risk of allergic sensitzation, especially IgE mediated sensitization, and its progression to clinical illness whereby allergic diseases such as asthma, eczema and allergic rhinitis and conjunctivitis may be prevented or treated. More precisely the present invention relates to the use of a particular virus in the manufacture of a pharmaceutical composition for preventing or treating a disease associated with allergic sensitization.

BACKGROUND OF THE INVENTION

The prevalence of allergic diseases has constantly increased in the developed countries during recent decades. The immune system of a newborn infant is immature, and develops during the first months and years of childhood. Healthy children develop an immune response against pathogens in their environment, whereas an increasing proportion of the children develop an allergic response against non-harmful factors in the environment leading to allergic diseases.

Several attempts have been made to prevent the development of allergic diseases. For many years exclusive breast-feeding, and avoidance of contact with possible allergenic sources such as cats and dogs in early childhood have been implicated as means for decreasing the risk of allergic diseases. However, the results have not been convincing.

A more recent hypothesis for the cause of allergic diseases is the "hygiene hypothesis", which is based on the fact that the prevalence of allergic diseases is significantly higher in prosperous countries with high standards of living and hygiene, than in countries having lower standards of hygiene. Further an inverse association between the number of siblings and allergic diseases has been documented in epidemiological surveys [1,2]. Growing up on a farm seems to be associated with a lower prevalence of allergic rhinitis and sensitization [3, 4, 5]. Children who do not live on a farm but have regular contact with livestock had also a lower prevalence of allergic sensitization [4]. The underlying reasons behind these associations are largely unknown, but the "hygiene hypothesis" provides a possible explanation suggesting that exposure to a variety of microbes in childhood protects against allergic diseases by promoting the maturation of the immune system [2,6]. One possible approach to tackle allergy has been the administration of probiotic bacteria, especially lactic acid bacteria, which have been shown to promote a tolerogenic immune response.

Several studies have suggested a role for Th2-polarized CD4+ T cells in the pathogenesis of asthma and allergy [7-9] but the exact immunological mechanisms regulating allergic sensitization are not known. Th1-biased immune responses may down-regulate the effects of Th2 cells [7] or regulatory T cells may control the function of both Th1 and Th2 cells as well as the Th1/Th2 balance [8, 9]. Although some reports are contradictory, there is epidemiological support that some infections, such as hepatitis A virus (HAV) [10-13], *Toxoplasma gondii* [12, 13] and *Helicobacter pylori* [12-14] and bacterial components [15-17] are associated with a reduced risk of allergic diseases, thus supporting the hypothesis that the microbial load is an important environmental factor conferring protection against the development of allergies in childhood [18]. Moreover, an independent inverse association was observed between the number of gastrointestinal infections before the age of 5 years and the risk of atopy in the UK [19]. It has also been reported that early childhood infection with human herpes virus type 6 (HHV-6) could protect against the development of IgE sensitization, atopic disease and allergy in young children (WO2006/031195).

However, not all microbial infections have a protective effect on the prevalence of atopic diseases. It was for example found that seropositivity for intestinal bacterial pathogens such as *Clostridium difficile, Campylobacter jejuni* and *Yersinia enterocolitica* was associated with a higher prevalence of atopy among Danish adults [13]. Recently Benn et al. reported that infectious diseases during the first 6 months of life (mostly upper respiratory infections) increase the risk of atopy [20], and Bager and collaborators observed a growing risk of atopy with increasing number of infections caused by airborne viruses (measles, rubella, mumps and varicella) before the age of 1 year [21].

There is a definite need of effective means for decreasing the risk of allergic sensitization and thereby preventing or treating diseases associated therewith. In particular there is a need of preventing the development of allergic diseases such as asthma, eczema, allergic rhinitis and conjunctivitis and food-induced allergies. The present invention meets these needs.

BRIEF DESCRIPTION OF THE INVENTION

The present invention is based on the use of enterovirus for preventing or treating a disease associated with allergic sensitization. In particular the invention provides the use of enterovirus in the manufacture of a pharmaceutical composition for preventing or treating a disease associated with allergic sensitization, wherein said enterovirus does not contain an exogenous nucleic acid sequence that is integrated into the viral genome and that encodes an allergen that induces said allergic sensitization. A method of preventing or treating a disease associated with allergic sensitization, wherein an effective amount of a pharmaceutical composition comprising enterovirus is administered to a person in need thereof, is also disclosed, and wherein said enterovirus does not contain an exogenous nucleic acid sequence that is integrated into the viral genome and that encodes an allergen that induces said allergic sensitization.

Particular implications of the invention are set forth in the dependent claims. Other objects, details and advantages will become apparent from the following detailed description.

Figure 1:
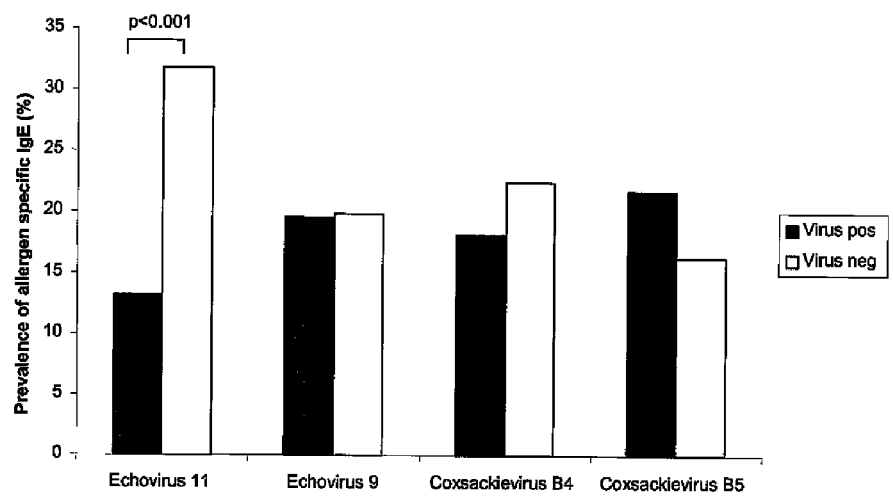
FIG. 1 shows the prevalence of allergen-specific IgE in Russian Karelian children according to seropositivity for different enterovirus serotypes.

Results are shown as relative expression of IL-10 mRNA compared to medium-treated cells. EV=enterovirus.

DETAILED DESCRIPTION OF THE INVENTION

The invention is based on the finding that allergic sensitization and diseases associated therewith may be prevented by vaccinating with a composition comprising enteroviruses as an immunoactive ingredient. Recombinant viruses comprising an exogenous nucleic acid sequence, which is integrated into the viral genome, and which encodes an epitope of an allergen and an artificial proteolytic cleavage site have previously been suggested as vaccines against allergy (WO93/11251) even though no examples proving the effect against allergy were given. The approach is completely different from the present invention, because the virus functions as a passive "carrier" or delivery vehicle for the exogenous nucleic acid integrated into the viral genome and coding for an antigen, which is believed to elicit a desired immune response against said antigen, whereas the present invention is based on the immunoregulatory effect which is induced by the enterovirus itself. Therefore the enterovirus of the present invention is the active component and it contains no integrated exogenous nucleic acid sequence that encodes an allergen that induces the allergic sensitization to be prevented or treated. However, the enterovirus used in the present invention may include a non-coding exogenous nucleic acid sequence, which is integrated into the viral genome, as well as coding or non-coding exogenous nucleic acid, which is not integrated into the viral genome. The enterovirus used in the present invention may also include exogenous proteins. In one embodiment of the invention the enterovirus contains no exogenous nucleic acid that encodes exogenous protein, and especially it contains no integrated exogenous nucleic acid that encodes exogenous protein.

"Allergen" as used herein is a compound that may induce an allergic immune response, and it may be a whole protein or only an immunoactive fragment i.e. epitope thereof. Nucleic acids are clearly not considered allergens in this connection.

The group of enteroviruses includes more than 100 different serotypes. Enterovirus infections are usually subclinical, but they may also cause various kinds of diseases. Polioviruses, coxsackie B-, coxsackie A-, and echo-virus as well as numbered enteroviruses are enteroviruses known to be involved in the development of a variety of diseases. Enterovirus infections are spreading through the fecal-oral route and infect the host via the mucosal and gut-associated immune system. They are potent activators of the immune system and cause strong changes in the immune system.

"Enterovirus" as used herein includes both whole enteroviruses as well as components thereof or their combinations. The enterovirus may be an attenuated or non-attenuated live enterovirus strain, a genetically modified strain, or a component derived from an enterovirus strain, such as a subunit or peptide, a structural protein component or their combination, such as a virus like particle, or a genome or genome fragment, such as RNA or cDNA encoding an immunologically active viral protein. It may also be a killed i.e. an inactivated enterovirus strain.

Enteroviruses which are particularly useful in the prevention and treatment of allergic sensitization can be identified by their ability to induce immunoregulatory pathways or to down-regulate Th2-type immune responses. Such enteroviruses can be identified by analyzing their effect on regulatory T-cells and/or Th1/Th2-balance and/or production of immunoregulatory cytokines such as IL-10 either during in vitro stimulation of peripheral blood leukocytes with different enteroviruses or in vivo in children with enterovirus infection. Typically such enteroviruses should activate FoxP3-positive regulatory T cells or regulatory T cells which produce IL-10 or other immunoregulatory cytokines. Such enteroviruses may also decrease the activity of Th2-type cells reflected e.g. by a decrease in the production of IL-4 or other Th2-type cytokines and/or paralleling increase in the activity of Th1-type cells and increased production of interferon-gamma or other Th1-type cytokines. Enteroviruses, which are particularly useful in this invention, can also be identified by their protective effect in epidemiological studies. Typically such enteroviruses should have been more frequent in individuals who have not developed allergic sensitization or allergic symptoms compared to subjects who have developed allergic sensitization or allergic symptoms. These viruses can be identified by measuring serotype specific antibodies from blood or by analyzing the antigenic or genetic properties of viruses detected in this kind of epidemiological studies.

Attenuated viruses are viruses of which the virulence has been reduced. This may be carried out by different methods including serial passage of the virus in cell cultures, antigenic modification by chemical treatments, construction of recombinant or chimeric viruses, mutagenization of viral genome, deletion or insertion of certain gene regions, selection of temperature sensitive mutants or irradiation. Alternatively, the enteroviruses may be attenuated natural virus isolates or infectious virus cDNA or RNA having reduced capability to cause clinical disease.

The live attenuated or non-attenuated enterovirus is conveniently administered orally. Each immunizing dose includes infective viruses or infective RNA or cDNA in a titer, which is able to produce infection or activation of the innate or adaptive immune system or induce regulatory T-cells or regulatory cytokines in humans. This dose would correspond to that which is used in the traditional Sabin-type live oral poliovirus vaccine including a minimum of $10^{5.5}$-$10^6$ TCID$_{50}$ for poliovirus Type 1, $10^5$ TCID$_{50}$ for poliovirus type 2 and $10^{5.5}$-$10^{5.8}$ TCID$_{50}$ for poliovirus type 3 live attenuated Sabin strains of polioviruses. The dose may also be another, if it has been confirmed to be safe and infectious or able to activate the innate or adaptive immune system. (TCID=tissue culture infectious dose; TCID$_{50}$=the dose which infects 50% of the cultures.)

Alternatively, the enterovirus may include whole viruses, the infectivity of which has been inactivated, or subunit vaccines containing certain antigenic structures, proteins or peptides of the virus, or their combination (such as virus like particles), or fragments of viral RNA or cDNA encoding the whole virus or individual viral proteins or inactivated forms of the virus. Inactivated vaccines may be produced by propagating the virus in cell cultures and by purifying it from infected cells and culture media by high-speed centrifugation in a density gradient formed by sucrose or other high-density media. Alternatively the virus could be purified by chromatography. The infectivity of the purified viruses is destroyed by inactivating the viruses by chemical treatment (e.g. formalin inactivation like that used to produce IPV), irradiation or heat treatment. Subunit vaccines may consist of purified viral proteins or recombinant viral proteins, synthetic peptides corresponding to viral antigenic epitopes, virus like particles or empty viral capsids, which are produced during infection but lack the viral genome. These subunit vaccines can be administered either as such or conjugated to haptens or carriers (e.g. ISCOM particles, chitosan, TLR agonists, biodegradable microparticles).

The above mentioned enteroviruses can be given parenterally by injections, perorally, intradermally, transcutaneously, sublingually, intranasally, as inhalation, or per rectum. Each immunizing dose includes viral structures in a titer, which is able to induce proper immune response in humans. This dose would correspond to that used in Salk-type inactivated poliovirus vaccine including 1.8-2 µg of viral protein per each dose and 20-40 antigenic D-units of poliovirus type 1, 4-8 antigenic D-units of poliovirus type 2 and 16-32 antigenic D-units of poliovirus type 3. The dose may also be another, if it has been confirmed to be safe and immunogenic or able to stimulate the innate or adaptive immune system or induce regulatory T-cells or regulatory cytokines. Enteroviruses can be given in different combinations including one or more enterovirus serotypes given simultaneously or serially. If the different enteroviruses are given simultaneously the pharmaceutical composition may be in the form of a mixture of different enteroviruses. The enterovirus may also be given in combination with at least one allergen e.g. whole allergen or its immunologically active subunit in order to promote a tolerogenic response against said allergen. According to one embodiment of the invention the vaccine contains enteroviruses as the sole immunoactive ingredient, and according to another embodiment it contains a mixture of enteroviruses and one or more exogenous allergens.

The enterovirus is formulated into a pharmaceutical composition, which in addition to the active ingredients that elicit immune stimulation may comprise pharmaceutically acceptable excipients, carriers, haptens and adjuvants. Excipients, carriers, haptens and adjuvants may include for example phenoxyethanol, magnesium chloride, sucrose, thiomersal, formaldehyde, phenol, antibiotics (preservatives) or aluminium salts, polymer microparticles, ISCOM particles, carrier proteins (e.g. cholera toxin), liposomes, protein micelles (haptens/adjuvants), or TLR agonists.

The pharmaceutical composition is preferably administered to a child within 5 years after birth, and more preferably within 3 years, especially within 2 years, and most preferably within 1 year after birth, with boosters given later in life to prevent allergic sensitization. Individuals who have already been sensitized, regardless of symptoms of a disease or not, may be given the pharmaceutical composition at any age.

"An effective amount" of the pharmaceutical composition is an amount, which is able to elicit either an adaptive or innate immune response that is able to induce immunity and protect the recipient against the virus, either by eliciting neutralizing antibodies or a cell-mediated response, or both. It can also be an amount, which is able to induce production of regulatory cytokines (such as IL-10) or activate regulatory T-cells (Treg) or induce a favorable shift in the Th1/Th2 cell balance even if protective immunity against the virus is not induced. The induction of regulatory cytokines or cells or shift in Th1/Th2 balance can occur in virus-specific or allergen-specific immune responses or both. It can also be a more generalized effect to the immune system influencing a wide array of immune responses with different antigen or allergen specificities. Such a generalized effect is typically mediated by soluble immunoregulatory cytokines such as IL-10.

When the immune system is exposed to foreign components in the environment including pathogens, an immune response is induced, which may be dominated by either a Th1-type or Th2-type response. Both responses are fighting infections while Th2 cells are also promoting allergy. A proper balance between Th1/Th2 cells is essential for an appropriate response. However, in subjects susceptible to allergic diseases, the Th2-type response is dominating. In addition, these individuals may have abnormal function of regulatory T-cells and other components of immune regulation.

"Allergic sensitization" refers to eliciting a Th2 dominated immune response leading to production of allergen-specific IgE against various environmental antigens, mostly harmless ones. Allergen-specific IgE in turn mediates hypersensitivity reactions that provoke the symptoms of allergic disease. This kind of immune response may be measured by assaying allergen specific IgE e.g. from a blood sample. Elevated levels of allergen-specific IgE reflect allergic sensitization to a certain allergen. In addition, high levels of total IgE immunoglobulin may indicate allergic sensitization. Skin prick testing is also used for diagnosing allergic diseases. The pharmaceutical composition comprising enterovirus is a vaccine that is capable of preventing or treating any disease associated with allergic sensitization.

IgE mediated allergic sensitization may lead to various kinds of allergic diseases, such as allergic eczema, allergic asthma, IgE mediated food or drug allergy, allergic conjunctivitis or rhinitis. The enterovirus vaccine is capable of decreasing the risk of IgE mediated sensitization and thereby preventing diseases provoked by IgE sensitization, such as allergic rhinitis and asthma.

The enterovirus vaccine may be given to a whole birth cohort or a selected group of a population, such as children from families where at least one family member has been diagnosed with an allergic reaction or disease, to prevent allergic sensitization. In addition, the enterovirus vaccine can be used in individuals who have asymptomatic allergic sensitization (increased allergen-specific IgE concentrations without symptoms) to prevent them from developing clinical symptoms. In line with this, the enterovirus vaccine can also be used to relief allergic symptoms and disease.

Variations and associations in the prevalence of microbial infections and allergic sensitization in children in Finland and Russia were studied in a unique epidemiological setting in two socio-economically and culturally markedly different, although geographically adjacent areas.

Methods

Subject

The Russian Karelian study cohort included 266 schoolchildren, and the Finnish cohort likewise 266 schoolchildren. The children represented the mainstream populations and were not selected according to possible allergic or other diseases. All the children from the Karelian Republic had both parents of either Finnish or Karelian ethnicity, which confers an ethnic background close to that of the children in Finland [22]. The study cohorts included altogether 114 boys and 152 girls from each country. The mean age at sampling was 11.4 years (range 7-15 years) in both cohorts.

Blood samples were taken from altogether 1988 randomly selected schoolchildren in Karelia. The ethnic background of both the mother and father was recorded, and all children whose both parents were of either Finnish or Karelian ethnicity were included in the present study (N=266) For these Karelian children, a cohort of Finnish children was matched pairwise by age, gender, and time of the year of the sampling (no more than 1 month apart), thus minimizing the effect of the season on exposure to microbes and allergens. The Finnish cohort was recruited in the same way as the Karelian cohort and included initially 3654 school children living in the Oulu region of Finland [23]. Blood samples were taken from each child.

IgE and Virus Antibodies

The levels of allergen-specific IgE were measured using the Uni-CAP® fluoroenzyme immunoassay (Pharmacia Diagnostics, Uppsala, Sweden). Specific IgE for two common inhalant allergens (birch and cat) and for egg albumin was analyzed according to the manufacturers instructions.

These allergens were selected because the exposure to them can be expected to be quite similar in both populations. For allergen-specific IgE, values of 0.35 IU/l or more were considered positive. In previous studies total IgE values exceeding 100 IU/l have been considered as markers of atopic predisposition [24].

Group-reactive enterovirus antibodies were analyzed using enzyme immunoassay (EIA) and heat-treated coxsackievirus B4 (CBV4) as antigen as previously described [25]. This method detects antibodies which are not serotype specific but which are cross-reactive between several enterovirus serotypes. The ability of this method to detect cross-reactive antibodies against several serotypes was enhanced by heat-treating the virus antigen, as this treatment exposes hidden cross-reactive structures of the virus.

Antibodies, which are specific for a given serotype were measured using a plaque neutralising assay as previously described [26]. This method measures neutralising antibodies, which are specific for the serotype which is used in the assay. We screened antibodies against two coxsackievirus B serotypes (CBV4 and CBV5) and two echovirus serotypes (echovirus 9 and 11) using ATCC reference virus strains.

IgG class hepatitis A virus (HAV) antibodies were measured using Enzygnost® Anti HAV commercial EIA kit according to the manufacturer's instructions (Dade Behring, Marburg, Germany), Behring Elisa Processor III was used for further processing of the tests and for the calculation of the antibody levels.

Induction of Immunoregulatory Pathways

The effect of enterovirus on immunoregulatory pathways was analysed by stimulating mononuclear cell cultures with enterovirus. Peripheral blood mononuclear cells from healthy laboratory personnel were purified using BD Vacutainer® CPT™ Tube (BD, Franklin Lakes, N.J., USA) according to the manufacturer's instructions. Mononuclear cells were washed twice with RPMI 1640 (Gibco, Invitrogen, Carlsbad, Calif., USA) and cultured for 48 hours at +37° C. (5% $CO_2$) in round-bottom microtitre plate wells (Costar 96 well cell culture cluster, Corning Inc., Corning, N.Y., USA) using 200,000 cells per 100 µL per well. The culture medium contained 10% human serum, 1% penicillin, 1% streptomycin and 1% L-glutamin in RPMI 1640 and one of the following stimulants: Medium (control), infective enterovirus (coxsackievirus B4) (3 PFU/cell), highly purified and heat-treated CBV4 in 1.0 µg/ml concentration, dsRNA analog (TLR-3 agonist) poly(I:C) in 5 µg/ml concentration (Alexis Biochemicals, San Diego, Calif., USA), TLR7/8 agonist Resiquimod in 5 µg/ml concentration (Alexis Biochemicals), LPS from *E. coli* serotype J5 (Rc) as TLR4 agonist in 100 µg/ml concentration (Alexis Biochemicals) as well as a combination of soluble anti-CD3 and anti-CD28 antibodies (R&D Systems, Minneapolis, Minn., USA) as polyclonal T-cell activator.

The effect of virus on regulatory T cells was analysed by measuring the expression of FoxP3 and IL-10 specific mRNA. Analyses were done using RT-PCR and 7900 HT Fast real-time PCR system (Applied Biosystems, Foster City, Calif., USA). RNA was extracted with the RNeasy Mini Kit according to the manufacturer's instructions. During the RNA extraction, an on-column DNase digestion was performed with the RNase-Free DNase Set (Qiagen, Hilden, Germany). The RNA was reverse transcribed using the M-MLV reverse transcriptase enzyme and buffer (Promega, Madison, Wis., USA) and random hexamer primers. For real-time PCR assays, custom primers for FoxP3 and IL-10 were designed while primers for the housekeeping gene TATA box binding protein (TBP) were from a previous publication [27] with slight modification in the forward primer. Each primer set has one primer spanning the exon-exon border. The primer sequences were as follows: FoxP3 forward 5'-ACA GCA CAT TCC CAG AGT TCC-3', reverse 5'-GAA CTC CAG CTC ATC CAC G-3'; IL-10 forward 5'-CAG TTT TAC CTG GAG GAG GTG-3', reverse 5'-AGA TGC CTT TCT CTT GGA GCT TAT-3'; TBP forward 5'-CGA ATA TAA TCC CAA GCG GTT-3' and reverse 5'-ACT TCA CAT CAC AGC TCC CC-3'. The synthesized cDNA was amplified with the DyNAmo Flash SYBR Green qPCR Kit (Finnzymes, Espoo, Finland). Thermal cycling conditions were 7 min at 95° C., 40 cycles of 10 s at 95° C., 30 s at 60° C. and 30 s at 78° C. (for primer dimer elimination), followed by final extension at 60° C. for 1 min. A dissociation curve step ranging temperatures 60° C.-95° C. was added in the end of each run. For data analysis, the threshold cycle ($C_t$) values of FOXP3 and IL-10 were normalised to the $C_t$-values of the endogenous control gene TBP. Relative expression values were calculated using the Pfaffl method as previously described [28].

Statistical Methods

Statistical analyses were performed with the SPSS program version 12.0 (SPSS Inc., Chicago, Ill., USA) and Confidence Interval analyses (CIA) [29]. The prevalence of specific IgE, high values (>100 IU/l) of total IgE and microbial antibodies was compared between the two paired cohorts using McNemar's test. Comparisons of total IgE levels (continuous variable with a skewed distribution) between paired cohorts were performed using Wilcoxon Signed Ranks test. Cross-tabulation and Chi-square test or Fisher's exact test were applied for the analyses of associations between virus antibodies, high values of total IgE and specific IgE in Russian Karelia and Finland. Mann-Whitney U test was used when associations between total IgE levels and specific IgE (classified as positive or negative) were analysed and also in the analyses of associations between CBV4 IgG levels and specific IgE. As a multivariate technique, logistic regression was applied to identify the independent effect of each parameter when appropriate. The model selection was based on a forward stepwise procedure, where the limit to enter and to remove the term was equal to 0.10. The results are supported by the assessment of odds ratio (OR) and 95% confidence intervals (CI). If there were missing or indifferent values, cases were not included in the analyses involving those particular parameters. The number of such cases was small, for example, for microbial serologies in Russian Karelian children, 0-2 missing cases per each microbe analyzed. All analyses were two-sided. Statistically significant P-values (<0.05) are given.

Results

The prevalence of allergen-specific IgE was significantly lower in Russian Karelian children than in Finnish children (Table 1).

The prevalence of enterovirus and hepatitis A virus antibodies was significantly higher in children in Russian Karelia than in children in Finland (Table 2). In addition, in Russian Karelia allergic sensitization was rarer in children who had enterovirus antibodies while no such effect was seen in terms of hepatitis A antibodies (Table 3). Altogether 22% of the children who were enterovirus seronegative had at least one positive specific IgE result compared to 5% of seropositive children. The median enterovirus antibody level was 74 enzyme immunoassay units (EIU) (range: 0-224) in children who had no specific IgE compared to 49 EIU (range: 0-154) in those who had at least one allergen-specific IgE (P=0.048).

In Finland the number of HAV seropositive children was very low (Table 2) which made it difficult to analyze their association with allergen-specific IgE. However, enterovirus antibodies were frequent in the Finnish children, but in contrast to those in Russian Karelia, they showed no association with allergen-specific IgE responses (18% of the enterovirus seronegative children had at least one positive specific IgE result compared to 23% of the seropositive children).

The fact that an association between infections and prevalence of atopy was observed only in Russian Karelian children but not in the Finnish children can be explained by the assumption that Finnish children are infected at an older age, as the circulation of enteroviruses and other microbes is conspicuously lower in Finland. According to the hygiene hypothesis infections occurring during the first months of life are the most important ones, as at this age they can have a marked effect on the maturation of the gut-associated immune system and the developing regulatory pathways and Th1/Th2 balance.

In order to test if the protective effect of enteroviruses differs between different serotypes we analysed altogether 244 Russian Karelian children for allergen specific IgE and neutralising antibodies against four different enterovirus serotypes (CBV4, CBV5, echovirus 9 and echovirus 11). Since neutralising antibodies remain elevated for decades the presence of these antibodies indicates past infection by the serotype, which is used in the assay. Echovirus 11 was associated with strong protection against allergic sensitization (FIG. 1). Altogether 31.8% of echovirus 11 seronegative children had allergen-specific IgE against at least one of the three allergens shown in Table 1 compared to only 13.2% of echovirus 11 seropositive children (P<0.001). In multiple logistic regression analysis echovirus 11 seropositivity had a clear independent effect on allergen specific IgE (P<0.001; OR3.2 [95% CI 1.7-6.2]). The results indicate that the protective effect of enteroviruses against allergic sensitization may depend on the serotype of the virus.

The protective effect of enteroviruses against allergic sensitization may be mediated by their effect on the immune system. It is generally believed that development of allergic sensitization is related to abnormal immune regulation. Regulatory T cells play a major role in immune regulation and one possible mechanism by which virus could mediate the observed anti-allergic effect is virus-induced activation of these cells. Regulatory T cells specifically express transcription factor FoxP3 (natural regulatory T cells) and secrete immunoregulatory cytokines such as IL-10 (Tr1 regulatory cells). Particularly the secretion of IL-10 by Tr1 cells may be important in the down-regulation of allergic responses [30]. We analysed if enterovirus can stimulate regulatory cells by exposing peripheral blood mononuclear cells to infective enterovirus or heat-treated purified enteroviruses in vitro. Virus-induced response was compared to that obtained with TLR-agonists (poly(I:C), Resiquimod, *E. coli* LPS) and polyclonal T-cell activator (mixture of monoclonal anti-CD3 and anti-CD28 antibodies).

Figure 2:
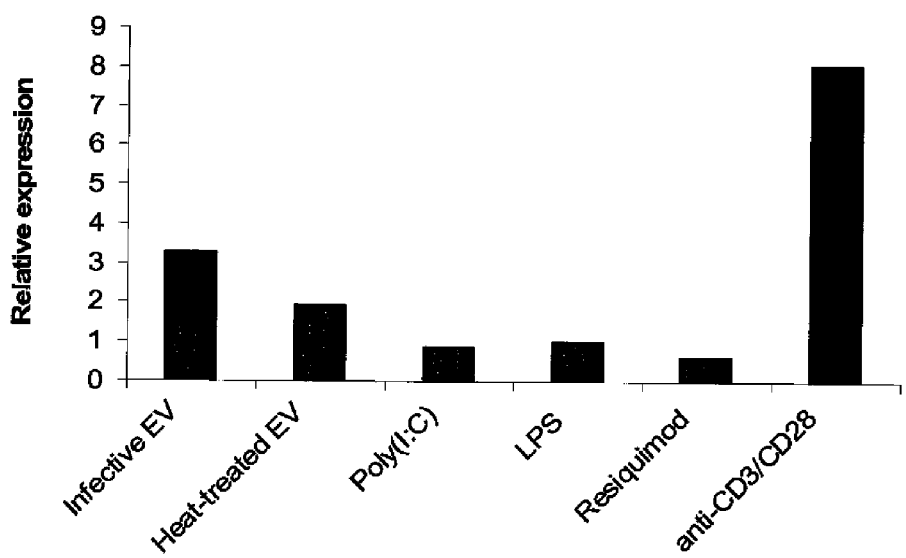
FIG. 2 shows the induction of FoxP3 mRNA in peripheral blood mononuclear cell cultures stimulated with infective enterovirus (CBV4), heat-treated purified enterovirus (CBV4), different TLR agonists (poly(I:C), LPS, Resiquimod) and polyclonal T-cell stimulator (anti-CD3+ anti-CD28). Cells were harvested after 24-hour incubation. Results are shown as relative expression of FoxP3 mRNA compared to medium-treated cells. EV=enterovirus.
Figure 3:
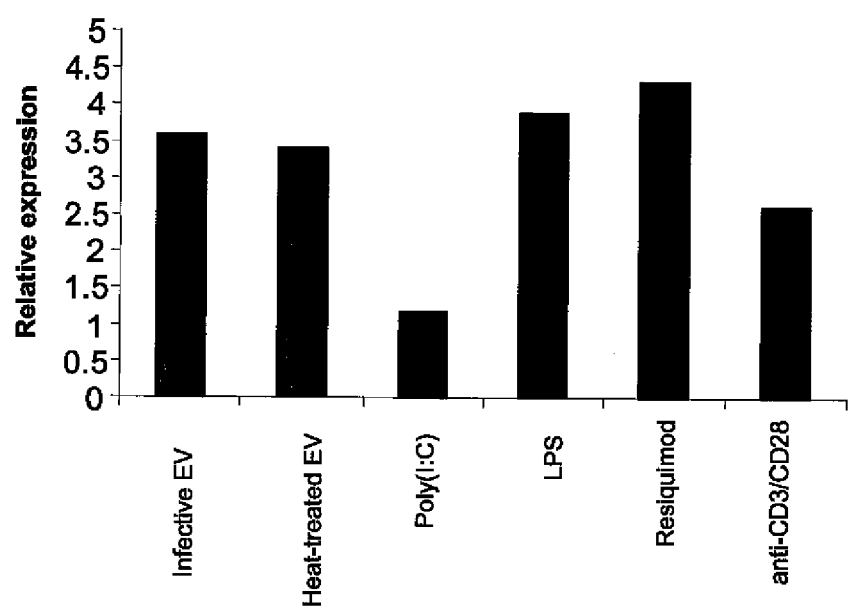
FIG. 3 shows the induction of IL-10 mRNA in peripheral blood mononuclear cell cultures stimulated with infective enterovirus (CBV4), heat-treated purified enterovirus (CBV4), different TLR agonists (poly(I:C), LPS, Resiquimod) and polyclonal T-cell stimulator (anti-CD3+ anti-CD28). Cells were harvested after 24-hour incubation.

Exposure of mononuclear cells to infective CBV4 led to a clear (3.3-fold) increase in the expression of FoxP3 specific mRNA (FIG. 2) and 3.6-fold increase in IL-10 specific mRNA compared to mock-treated cultures (FIG. 3). Similarly, heat-treated CBV4 resulted in a 1.9-fold increase in FoxP3 mRNA and 3-fold increase in IL-10 mRNA. Poly(I:C) did not induce either FoxP3 or IL-10 mRNA, while the anti-CD3/anti-CD28 combination induced the expression of both FoxP3 and IL-10 (8.1- and 2.6-fold increases, respectively). Resiquimod and LPS did not induce FoxP3 expression (FIG. 2) but resulted in a clear increase in IL-10 expression. These results show that enteroviruses are able to activate regulatory T cells. Enterovirus-induced activation was comparable to that obtained using a strong polyclonal T-cell activator (anti-CD3/anti-CD28 mixture) supporting the biological relevance of this phenomenon. Furthermore, enterovirus was able to induce stronger FoxP3 expression than the three classical TLR agonists and as strong IL-10 expression as TLR4 and TLR7/8 agonists (LPS and Resiquimod, respectively).

Thus, these results suggest that enterovirus infections are associated with a decreased risk of allergic sensitzation and can modulate the immune system in a way, which can stimulate immunoregulatory pathways and thereby protect against allergic diseases.

TABLE 1

The prevalence (% and 95% CI) of allergen-specific IgE in schoolchildren in Finland and Russian Karelia

|  | Finland (n = 266) | Russian Karelia (n = 266) | P value |
| --- | --- | --- | --- |
| Cat | 11% (8-16%) | 2% (1-5%) | <0.001 |
| Birch | 11% (8-16%) | 2% (1-5%) | <0.001 |
| Egg albumen | 6% (4-10%) | 3% (2-6%) | 0.093 |
| At least one positive | 22% (17-27%) | 6% (4-10%) | <0.001 |

TABLE 2

Prevalence (% and 95% CI) of enterovirus and hepatitis A virus antibodies in schoolchildren in Finland and Russian Karelia

|  | Finland (n = 266) | Russian Karelia (n = 266) | P value |
| --- | --- | --- | --- |
| Enterovirus | 77% (72-82%) | 93% (90-96%) | <0.001 |
| Hepatitis A virus | 2%* (1-5%) | 24% (19-29%) | <0.001 |

Only 166 Finnish children were screened for HAV antibodies
Enterovirus antigen used in this assay was highly purified Coxsackievirus B4 which was heat-treated to make it broadly reactive with antibodies against different enterovirus serotypes.

TABLE 3

Proportion of children (% and 95% CI) positive for at least one allergen-specific IgE in relation to seropositivity for enterovirus and hepatitis-A virus antibodies in schoolchildren in Russian Karelia

|  | Virus-seropositive | Virus-seronegative | P value | Logistic model* OR (95% CI) | P value |
| --- | --- | --- | --- | --- | --- |
| Enterovirus | 13/247 (5%; 3-9%) | 4/18 (22%; 9-45%) | 0.02 | 0.16 (0.04-0.6) | 0.006 |
| Hepatitis A Virus | 5/63 (8%; 3-17%) | 12/201 (6%; 3-10%) | 0.579 |  | NS |

NS, not significant.
*a forward stepwise model (p for entry and removal 0.10)

REFERENCES

1. Karmaus W. Botezan C. Does a higher number of siblings protect against the development of allergy and asthma? A review. J Epidemiol Community Health 2002; 56:209-217.
2. Strachan D P. Family size, infection and atopy: The first decade of the "hygiene hypothesis". Thorax 2000; 55 Suppl 1:S2-10.
3. von Hertzen L, Mäkelä M, Petäys T, et al. Growing disparities in atopy between the Finns and the Russians: A comparison of 2 generations. J Allergy Clin Immunol 2006; 117:151-157.
4. Riedler J, Eder W, Oberfeld G, Schreuer M. Austrian children living on a farm have less hay fever, asthma and allergic sensitization. Clin Exp Allergy 2000; 30:194-200.

5. Kilpelainen M, Terho E O, Helenius H, Koskenvuo M. Farm environment in childhood prevents the development of allergies. Clin Exp Allergy 2000; 30:201-208.
6. Strachan D P. Hay fever, hygiene, and household size. BMJ 1989; 299:1259-60.
7. Mosmann T R, Sad S. The expanding universe of T-cell subsets: Th1, Th2 and more. Immunol Today 1996; 17:138-146.
8. Umetsu D T, Akbari O, Dekruyff R H. Regulatory T cells control the development of allergic disease and asthma. J Allergy Clin Immunol 2003; 112:480-487.
9. Curotto de Lafaille M A, Lafaille J J. CD4(+) regulatory T cells in autoimmunity and allergy. Curr Opin Immunol 2002; 14:771-778.
10. McIntire J J, Umetsu S E, Macaubas C, et al. Immunology: Hepatitis A virus link to atopic disease. Nature 2003; 425:576.
11. Matricardi P M, Rosmini F, Ferrigno L, et al. Cross sectional retrospective study of prevalence of atopy among Italian military students with antibodies against hepatitis A virus. BMJ 1997; 314:999-1003.
12. Matricardi P M, Rosmini F, Riondino S, et al. Exposure to food-borne and orofecal microbes versus airborne viruses in relation to atopy and allergic asthma: Epidemiological study. BMJ 2000; 320:412-417.
13. Linneberg A, Ostergaard C, Tvede M, et al. IgG antibodies against microorganisms and atopic disease in Danish adults: The Copenhagen allergy study. J Allergy Clin Immunol 2003; 111:847-853.
14. Kosunen T U, Hook-Nikanne J, Salomaa A, Sarna S, Aroma A, Haahtela T. Increase of allergen-specific immunoglobulin E antibodies from 1973 to 1994 in a Finnish population and a possible relationship with *helicobacter pylori* infections. Clin Exp Allergy 2002; 32:373-378.
15. Gereda J E, Leung D Y, Liu A H. Levels of environmental endotoxin and prevalence of atopic disease. JAMA 2000; 284:1652-1653.
16 Gereda J E, Leung D Y, Thatayatikom A, et al. Relation between house-dust endotoxin exposure, type 1 T-cell development, and allergen sensitisation in infants at high risk of asthma. Lancet 2000; 355:1680-1683.
17. von Mutius E, Braun-Fahrlander C, Schierl R, et al. Exposure to endotoxin or other bacterial components might protect against the development of atopy. Clin Exp Allergy 2000; 30:1230-1234.
18. Matricardi P M, Ronchetti R. Are infections protecting from atopy? Curr Opin Allergy Clin Immunol. 2001; 1:413-419.
19. Cullinan P, Harris J M, Newman Taylor A J, et al. Can early infection explain the sibling effect in adult atopy? Eur Respir J 2003; 22:956-961.
20. Benn C S, Melbye M, Wohlfahrt J, Bjorksten B, Aaby P. Cohort study of sibling effect, infectious diseases, and risk of atopic dermatitis during first 18 months of life. BMJ 2004; 328:1223.
21. Bager P, Westergaard T, Rostgaard K, Hjalgrim H. Melbye M. Age at childhood infections and risk of atopy. Thorax 2002; 57:379-382.
22. Kondrashova A, Romanov A, Reunanen A, et al. A sixfold gradient in the incidence of type I diabetes at the eastern border of Finland—evidence of a critical role of environment in the disease pathogenesis. Ann Med 2005; 37:67-72.
23. Mäki M, Mustalahti K, Kokkonen J, et al. Prevalence of celiac disease among children in Finland. N Engl J Med 2003; 348:2517-2524.
24. Vartiainen E, Petays T, Haahtela T, Jousilahti P, Pekkanen J. Allergic diseases, skin prick test responses, and IgE levels in North Karelia, Finland, and the Republic of Karelia, Russia. J Allergy Clin Immunol 2002; 109:643-648.
25. Salminen K, Sadeharju K, Lönnrot M, et al. Enterovirus infections are associated with the induction of beta-cell autoimmunity in a prospective birth cohort study. J Med Virol 2003; 69:91-98.
26. Roivainen M, Knip M, Hyöty H. et al. Several different enterovirus serotypes can be associated with prediabetic autoimmune episodes and onset of overt IDDM. Childhood Diabetes in Finland (DiMe) Study Group. J Med. Virol. 1998; 56:74-8.
27. Isomäki P et al, The expression of SOCS is altered in rheumatoid arthritis, Rheumatology 2007: 46:1538-46.
28. Pfaffl M W, A new mathematical model for relative quantification in real-time RT-PCR, Nucleic Acids Research 2001; 29: 2002-2007.
29. Altman D, Altman D G, Bryant T, Gardner M, Gardner M J, Machin D. Statistics with Confidence. London: BMJ Books, 2000.
30. Wu K, Bi Y, Sun K, Wang C. IL-10-producing type 1 regulatory T cells and allergy. Cell Mol Immunol. 2007; 4:269-75.

The invention claimed is:

1. A method for reducing a risk of contracting an IgE mediated allergic sensitization and developing an IgE-mediated allergic disease, comprising steps of 1). selecting a person from the group consisting of a child from a family where at least one family member has been diagnosed with an IgE mediated allergic reaction or IgE-mediated disease, an individual who has an IgE-mediated asymptomatic allergic sensitization and an individual having an IgE-mediated allergic symptom and IgE-mediated disease, and 2). administering an effective amount of a pharmaceutical composition comprising enterovirus, wherein said enterovirus does not contain an exogenous nucleic acid sequence that is integrated into the viral genome and encodes an allergen that induces said allergic sensitization and disease.

2. The method of claim 1, wherein the pharmaceutical composition comprises the enterovirus selected from a live enterovirus strain, a genetically modified enterovirus strain, an inactivated enterovirus strain, a structural component of an enterovirus strain, and a combination thereof.

3. The method of claim 1, wherein the enterovirus is selected from a virus-like particle, the genome or a fragment of the genome of an enterovirus strain.

4. The method of claim 1, wherein the pharmaceutical composition is administered perorally, intracutaneously, transcutaneously, sublingually, intranasally, by inhalation, rectally, or parenterally.

5. The method of claim 1, wherein the disease is asthma, allergic eczema, food or drug allergy, or allergic rhinitis or conjunctivitis.

6. The method of claim 1, wherein the child is within 2 years after birth.

7. The method of claim 1, wherein pharmaceutical compositions comprising different enterovirus serotypes are given either simultaneously or serially.

8. The method of claim 1, wherein the pharmaceutical composition is administered in combination with an allergen.

* * * * *